/ United States Patent (12)
Bischoff et al.

(10) Patent No.: US 7,274,465 B2
(45) Date of Patent: Sep. 25, 2007

(54) OPTICAL METROLOGY OF A STRUCTURE FORMED ON A SEMICONDUCTOR WAFER USING OPTICAL PULSES

(75) Inventors: Joerg Bischoff, Illmenau (DE); Junwei Bao, Fremont, CA (US)

(73) Assignee: Timbre Technologies, Inc., Santa Clara, CA (US)

( * ) Notice: Subject to any disclaimer, the term of this patent is extended or adjusted under 35 U.S.C. 154(b) by 36 days.

(21) Appl. No.: 11/061,330

(22) Filed: Feb. 17, 2005

(65) Prior Publication Data

US 2006/0181713 A1   Aug. 17, 2006

(51) Int. Cl.
*G01B 11/02* (2006.01)
*G01B 9/02* (2006.01)

(52) U.S. Cl. .................. 356/511; 356/450; 356/521
(58) Field of Classification Search ............. 356/498, 356/499, 511, 512, 521, 600, 601, 625, 450
See application file for complete search history.

(56) References Cited

U.S. PATENT DOCUMENTS 5,033,853 A *  7/1991 Frangineas, Jr. ............ 356/450
5,748,317 A *  5/1998 Maris et al. ................. 356/502
6,137,570 A * 10/2000 Chuang et al. ........... 356/237.5
6,256,100 B1 *  7/2001 Banet et al. ................. 356/432
6,633,386 B2 * 10/2003 Walmsley et al. .......... 356/450
6,785,638 B2 *  8/2004 Niu et al. .................... 702/189
6,891,626 B2    5/2005 Niu et al.
6,943,900 B2 *  9/2005 Niu et al. .................... 356/625
2004/0267397 A1 * 12/2004 Doddi et al. ................ 700/110

OTHER PUBLICATIONS

Li, L. (1996). "Formation and Comparison of Two Recursive Matrix Algorithms For Modeling Layered Diffraction Gratings," *J. Opt. Soc. Am.* A13: 1024-1035.
Cheriaux, G. et al. (2001). "Ultra-Short High-Intensity Laser Pulse Generation and Amplification," *Meas. Sci. Technol.* 12:1769-1776.
APE-Berlin (2004). "Technical Description of SPIDER".
Kruger, A. (May 2004). "Getting Practical," *SPIE OE Magazine*, pp. 23-25.
Uibernacker, M. (May 2004). "Pulsed Lasers Speed Up," *SPIE OE Magazine*, pp. 18-22.
Staudt, P. (APE-Berlin). (Sep. 2004). "Getting The Measure of Ultrashort Pulses," *SPIE OE Magazine*, pp. 33-35.

* cited by examiner

*Primary Examiner*—Gregory J. Toatley, Jr.
*Assistant Examiner*—Michael A Lyons
(74) *Attorney, Agent, or Firm*—Morrison & Foerster LLP (57) ABSTRACT

A structure formed on a wafer can be examined by directing an incident pulse at the structure, the incident pulse being a sub-picosecond optical pulse. A diffraction pulse resulting from the incident pulse diffracting from the structure is measured. A characteristic of the profile of the structure is then determined based on the measured diffraction pulse.

27 Claims, 10 Drawing Sheets

OPTICAL METROLOGY OF A STRUCTURE FORMED ON A SEMICONDUCTOR WAFER USING OPTICAL PULSES

BACKGROUND

1. Field

The present application relates to optical metrology, and more particularly to optical metrology of structures formed on semiconductor wafers using optical pulses.

2. Related Art

Optical metrology involves directing an incident beam at a structure, measuring the resulting diffracted beam, and analyzing the diffracted beam to determine a feature of the structure. In semiconductor manufacturing, optical metrology is typically used for quality assurance. For example, after fabricating a periodic grating in proximity to a semiconductor chip on a semiconductor wafer, an optical metrology system is used to determine the profile of the periodic grating. By determining the profile of the periodic grating, the quality of the fabrication process utilized to form the periodic grating, and by extension the semiconductor chip proximate the periodic grating, can be evaluated.

In conventional optical metrology, the diffraction response versus the light wavelength is typically measured. The spectral decomposition of the light can be done either in the incident light path or in the reflected light path. To this end, a monochromator is typically used, which is based on the light dispersion by a prism or a grating. The dispersed light then can be directed to a detector-array such as a charge coupled device (CCD) array, or it can be moved consecutively swept over one detector. In the first case, the accuracy is limited due to the tolerances throughout the detector elements. In the second case, the measurement time is increased due to the motion.

SUMMARY

In one exemplary embodiment, a structure formed on a wafer can be examined by directing an incident pulse at the structure, the incident pulse being a sub-picosecond optical pulse. A diffraction pulse resulting from the incident pulse diffracting from the structure is measured. A characteristic of the profile of the structure is then determined based on the measured diffraction pulse.

DESCRIPTION OF DRAWING FIGURES

The present application can be best understood by reference to the following description taken in conjunction with the accompanying drawing figures, in which like parts may be referred to by like numerals:

FIGS. 7-A to 7-D depict time shifting of an incident pulse;

FIGS. 8-A to 8-D depict amplitude changes of an incident pulse;

FIGS. 9-A to 9-D depict phase changes of an incident pulse;

FIGS. 10-A to 10-D depict second order amplitude change of an incident pulse;

FIGS. 12-A to 12-E depict hypothetical profiles of a structure;

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

1. Optical Metrology using Optical Pulses

Figure 1:
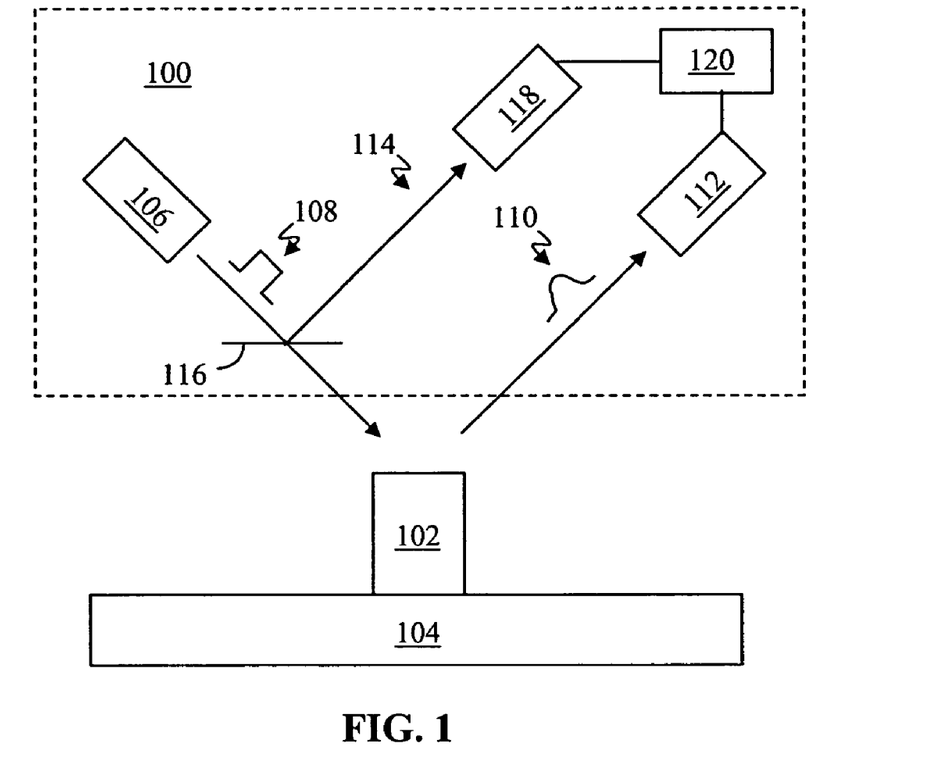
FIG. 1 depicts an exemplary optical metrology system.

With reference to FIG. 1, an optical metrology system 100 can be used to examine and analyze a structure 102 formed on a wafer 104. For example, optical metrology system 100 can be used to determine a feature of a periodic grating formed on wafer 104. As described earlier, the periodic grating can be formed in test areas on wafer 104, such as adjacent to a device formed on wafer 104. Alternatively, the periodic grating can be formed in an area of the device that does not interfere with the operation of the device or along scribe lines on wafer 104.

In one exemplary embodiment, optical metrology system 100 includes a pulse generator 106, which directs an incident pulse 108 at structure 102. In the present exemplary embodiment, incident pulse 108 is a sub-picosecond optical pulse. Optical metrology system 100 includes a pulse detector 112, which measures a diffraction pulse 110 resulting from incident pulse 108 diffracting from structure 102. Optical metrology system 100 also includes a processor 120, which determines a characteristic of the profile of structure 102 based on diffraction pulse 110.

As will be described in greater detail below, in one exemplary embodiment, a characteristic of the profile of structure 102 is determined by comparing the measured diffraction pulse to a simulated diffraction pulse, which is associated with a hypothetical profile of structure 102. When the pulses match within a matching criterion, the hypothetical profile of structure 102 associated with the simulated diffraction pulse is used to determine a characteristic of the profile of structure 102.

In another exemplary embodiment, a measured diffraction spectrum is derived from the measured diffraction pulse. The measured diffraction spectrum is compared to a simulated diffraction spectrum, which is associated with a hypothetical profile of structure 102. When the spectra match within a matching criterion, the hypothetical profile of structure 102 associated with the simulated diffraction spectrum is used to determine a characteristic of the profile of structure 102.

2. Pulse Generator

In one exemplary embodiment, pulse generator 106 can be an ultra-short pulse laser, such as a mode-locked, diode pumped Titanium-sapphire laser having pulse lengths in the femto-second (fs) range, a Ytterbium-Tungstate (Yb:KGW)-laser, and the like. See, Matthias Uibernacker: "Pulsed Lasers Speed Up", SPIE OE Magazine (May 2004) pp.

18-22; Arnd Krüger: "Getting Practical", SPIE OE Magazine (May 2004) pp. 23-25; and Gilles Cheriaux and Jean-Paul Chambaret, "Ultra-short high-intensity laser pulse generation and amplification", Meas. Sci. Technol. 12 (2001) 1769-1776. Pulse tuning (i.e., changing wavelength) can be achieved using an optic parametric amplifier (OPA). In the present exemplary embodiment, a wavelength range from 240 nm through 10 µm can be swept.

3. Pulse Detector

As depicted in FIG. 1, incident pulse 108 diffracts from structure 102 as diffraction pulse 110, which is measured using pulse detector 112. As will be described in greater detail below, structure 102 can alter the shape of incident pulse 108. For example, when incident pulse 108 has a Gaussian envelope, incident pulse 108 can be stretched or compressed when diffracted from structure 102 as diffraction pulse 110. Structure 102 can also modulate the frequency of incident pulse 108, which is referred to as a "chirp."

After diffraction pulse 110 is measured, various techniques can be used to characterize diffraction pulse 110. For example, in a frequency domain, a spectrometer can be used to measure spectrum full width of half maximum (FWHM) bandwidth. In a time domain, an autocorrelator can be used to measure auto-correlation function (ACF) FWHM—pulse duration. In frequency and time domain, spectral phase interferometry (e.g., frequency-resolved optical grating (FROG), spectral phase interferometry for direct electric-field reconstruction (SPIDER), and the like) can be used to measure ACF and spectrum phase.

As noted above, auto-correlation can be applied in characterizing diffraction pulse 110 (i.e., diffraction pulse 110 is split and correlated with itself). Alternatively, cross-correlation can be applied (i.e., diffraction pulse 110 is correlated with a reference pulse). In the embodiment depicted in FIG. 1, a reference pulse 114 is obtained using a semi-transparent mirror 116 to split incident pulse 108. In the present exemplary embodiment, reference pulse 114 is measured using a second pulse detector 118. See also, Peter Staudt (APE-Berlin): "FROG—Upgrade for APE Autocorrelator Pulse Check", Powerpoint-Presentation 2004.

3.1 Spectrometer

As described above, in the frequency domain, a spectrometer can be used to measure spectrum FWHM bandwidth. In general, in a spectrometer, light going through an exit slit is recorded using a photoelectric detector. A spectrometer decomposes light into its wavelengths and determines the spectral intensity distribution of the light. A spectrometer typically includes an input collimator (input slit and input objective), an output optic (objective and exit slit), and a wavelength-selective element (e.g., a prism, a grating, or an interferometer) in between.

3.2 Auto-Correlator

As described above, in the time domain, an auto-correlator can be used to measure ACF FWHM—pulse duration. In general, the basic principle of an auto-correlator is to split diffraction pulse 110 into two pulses, time delay the two pulses, and superpose them. While sweeping the time delay, ACF can be recorded that corresponds to the intensity envelope of diffraction pulse 110. See also, Peter Staudt (APE-Berlin): "Getting the measure of ultrashort pulses", SPIE OE Magazine (September 2004) pp. 33-35.

3.3 Spectral Phase Interferometry

As described above, in frequency and time domain, spectral phase interferometry can be used to measure ACF and spectrum phase. See also, C. Iaconis and I. A. Walmsley: "Self Referencing Spectral Interferometry for Measuring Ultrashort Optical Pulses", Research Report Institute of Optics, Rochester University (provided by APE-Berlin) and C. Dorrer: "Characterization of Femtosecond Pulses with Phase and Amplitude Reconstruction using an Interferogram simultaneously with Spider" Research Report Laboratoire d'Optique Appliquée, Batterie de l'Yvette, 91761 Palaiseau Cedex, France (provided by APE-Berlin).

In one exemplary embodiment, spectral phase interferometry can be performed using a FROG option added to an autocorrelator system. In another exemplary embodiment, spectral phase interferometry can be performed using SPIDER. See also, APE-Berlin: "Technical Description of SPIDER", 2004.

In general, SPIDER includes generating two replicas of diffraction pulse 110 and delayed in time with respect to one another by $\tau$. For example, a Fabry-Perrot etalon can be used. A Fabry-Perrot etalon is a plane plate with both sides partly mirrored. This causes an incident pulse being split into two or more pulses (i.e., one pulse goes directly, while a second pulse is reflected first from the exit side back to the entrance side and from there again back into its original direction). Thus, the second pulse experiences an optical path delay by $2*d*n$, with d being the plate thickness and n the refraction index. This results in a time delay of $\Delta t = 2*d*n/c$, with c being the light velocity in vacuum.

After the two replicas are generated and delayed in time, a third pulse is stretched ("chirped") to a duration much longer than $\tau$. The two replicas are then mixed with the third pulse AC02 in a nonlinear medium ($\chi_{(N)}$). The resultant signal, $S(\omega_c)$, is resolved with a spectrometer.

A chirped pulse (i.e., the third pulse) is one in which the frequency (or color) of the pulse changes with time (much like the frequency (or pitch) of a bird's chirp increases in time). The chirped pulse is obtained with a dispersive delay line. For instance, a pair of gratings, a pair of prisms, or the material dispersion of glass can be used for this purpose.

The purpose of the nonlinear frequency mixing is to add a frequency shift to each of the two replicas. Since the two replicas are delayed in time with respect to one another, each is mixed in the nonlinear medium with a different quasi-monochromatic slice of the chirped pulse (i.e., the third pulse). Consequently, each of the replicas experience a slightly different frequency shift, resulting in a pair of frequency shifted pulses that are spectrally sheared with respect to one another.

A variety of techniques can be used to analyze the SPIDER data. One technique is derived from a procedure familiar from spatial interferometry. In particular, after a simple Fourier transform, filter, and inverse transform routine, a sampling of the spectral phase of the incident pulse is returned by concatenation (or box integration). Combining the sampled spectral phase with an independently measured spectral amplitude, and exploiting the Whittaker-Shannon sampling theory returns the time dependent intensity and phase of the pulse. See, Joseph Goodman, "introduction to Fourier Optics, McGraw Hill, 2. Edition, 1996.

4.0 Data Analysis

The following provides a brief mathematical formulation for performing optical metrology using optical pulses.

The electric field (E-field) of a pulse can be described as the integration of its spectral content $A(\omega)$ over the frequency range:

$$E(t) = \int_{-\infty}^{+\infty} A(\omega) \cdot e^{+i\omega t} d\omega. \qquad (1)$$

Due to this, E(t) and A(ω) are a pair of Fourier transforms. For the sake of simplicity assume that the pulse has a Gaussian shape:

$$E(t) = e^{+i\omega_0 t} \cdot e^{-\frac{1}{2}\left(\frac{t}{\tau}\right)^2}. \qquad (2)$$

Then, the spectrum A(ω) can be computed according to:

$$A(\omega) = \frac{1}{2\pi}\int_{-\infty}^{+\infty} E(t) \cdot e^{-i\omega t} d\omega = \frac{1}{2\pi}\int_{-\infty}^{+\infty} e^{-\frac{1}{2}\left(\frac{t}{\tau}\right)^2} \cdot e^{-i(\omega-\omega_0)t} d\omega. \qquad (3)$$

This integral can be solved by using a quadratic supplement resulting in:

$$A(\omega) = \frac{\tau}{\sqrt{2\pi}} \cdot e^{-\frac{(\omega-\omega_0)^2 \tau^2}{2}}. \qquad (4)$$

Because λ=c/2πω, the spectrum A(ω) can also be expressed as A(λ).

Assume for the sake of example that the wavelength $\lambda_0$ of the pulse is 400 nm. Further assume that the frequency range is limited by the 1/e drop leading to:

$$\omega - \omega_0 = \frac{2}{\tau}. \qquad (5)$$

The frequency bandwidth is then assumed to be 2(ω−ω₀). Then, with ω=2πν and the differentiation:

$$\Delta\lambda = 2\pi c \cdot \frac{\Delta\omega}{\omega_0^2} \qquad (6)$$

which can be derived to:

$$\tau = \frac{\lambda^2}{c \cdot \pi \cdot \Delta\lambda}. \qquad (7)$$

Then, assuming that the wavelength range to be covered is ±50 nm to 100 nm, the resulting value for τ is approximately 10 fs. In order to cover a larger spectral range, the measurement can be performed for two or more wavelengths, e.g., with a tunable laser. A coarse general estimation (that applies to a general pulse shape) is Δω·Δt=1.

4.1 Numerical Approach

The following describes a numerical approach to analyzing the interaction of an incident pulse with a structure.

Assume the incident pulse (i.e., the E-field of the pulse) is given as a function of time $E_0(t)$. Assume the impulse response G(t−τ) (i.e., the reaction on a Dirac-impulse of the structure) is known. Then, the E-field dependency of the diffraction pulse can be described as a convolution:

$$E(\tau) = E_0(t) * G(t-\tau). \qquad (8)$$

In the frequency domain, the convolution operation becomes a multiplication:

$$E(v) = E_0(v) \cdot G(v). \qquad (9)$$

Here, $E_0(v)$ and E(v) are the incident and the diffraction spectrum, and G(v) is the frequency response of the structure. The spectra X(v) and the time functions X(t) are pairs of Fourier transforms (X=E, $E_0$, G).

In particular, the impulse response G(t−τ) is the Fourier transform of the frequency response (i.e., of the spectral response of the structure):

$$G((t-\tau)) = F(G(v)) \qquad (10)$$

with v being the light frequency. Since the wavelength λ corresponds to c/v, this corresponds to the spectral response and G(v) can be easily translated into G(λ). The spectral response G(λ) can be generated using a numerical analysis technique, such as rigorous coupled wave analysis (RCWA), a machine learning system, and the like.

Figure 2:
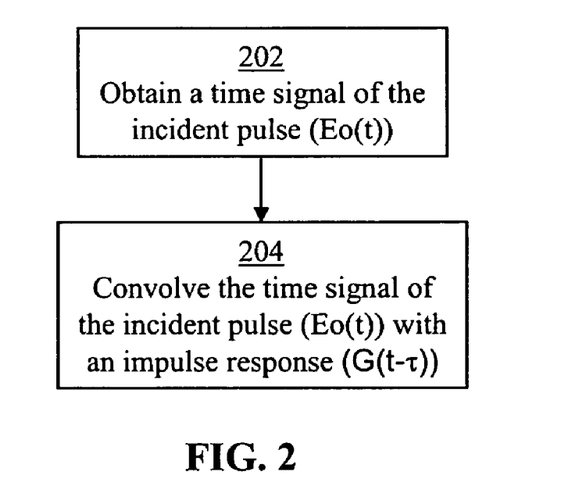
FIG. 2 depicts an exemplary process to compare a measured diffraction pulse with a simulated diffraction pulse.

In one exemplary embodiment, in the time domain, the pulse shape of the measured diffraction pulse is compared with a simulated diffraction pulse. In particular, with reference to FIG. 2, an exemplary process is depicted to compare a measured diffraction pulse with a simulated diffraction pulse. In 202, a time signal of the incident pulse ($E_0(t)$) is obtained. In 204, the time signal of the incident pulse ($E_0(t)$) is convolved with an impulse response (G(t−τ)) of the structure to generate the simulated diffraction pulse.

Figure 3:
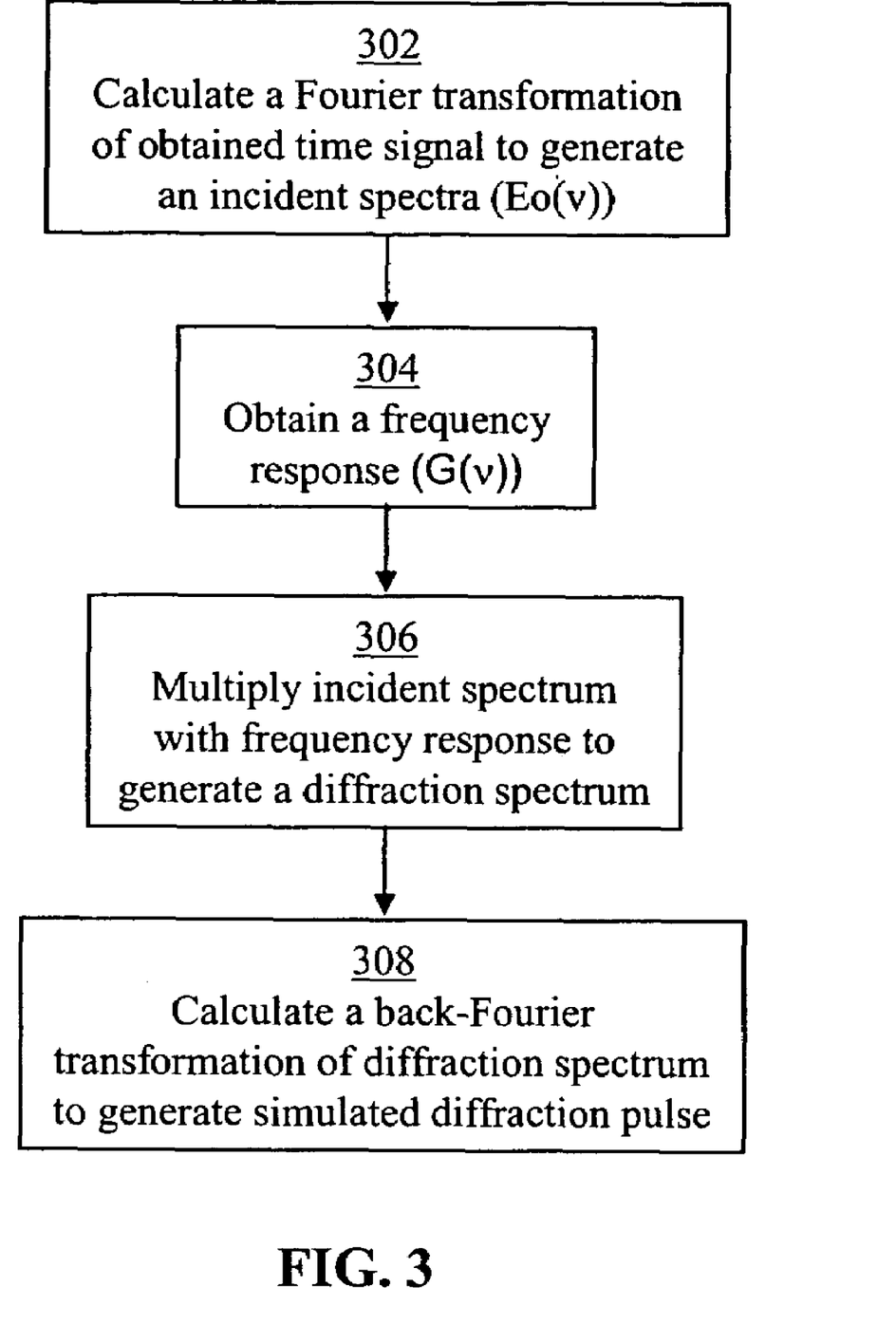
FIG. 3 depicts an exemplary convolution process.

With reference to FIG. 3, an exemplary convolution process is depicted. In 302, a Fourier transformation of the obtained time signal is calculated to generate an incident spectrum ($E_0(v)$). In 304, a frequency response (G(v)) of the structure is obtained. In 306, the incident spectra ($E_0(v)$) is multiplied with the frequency response (G(v)) to generate a diffraction spectrum (E(v)). In 308, a back-Fourier transformation of the diffraction spectrum (E(v)) is calculated to generate the simulated diffraction pulse.

In another exemplary embodiment, in the frequency domain, a measured diffraction spectrum is derived from the measured diffraction pulse. The measured diffraction spectrum is compared to a simulated diffraction spectrum.

Figure 4:
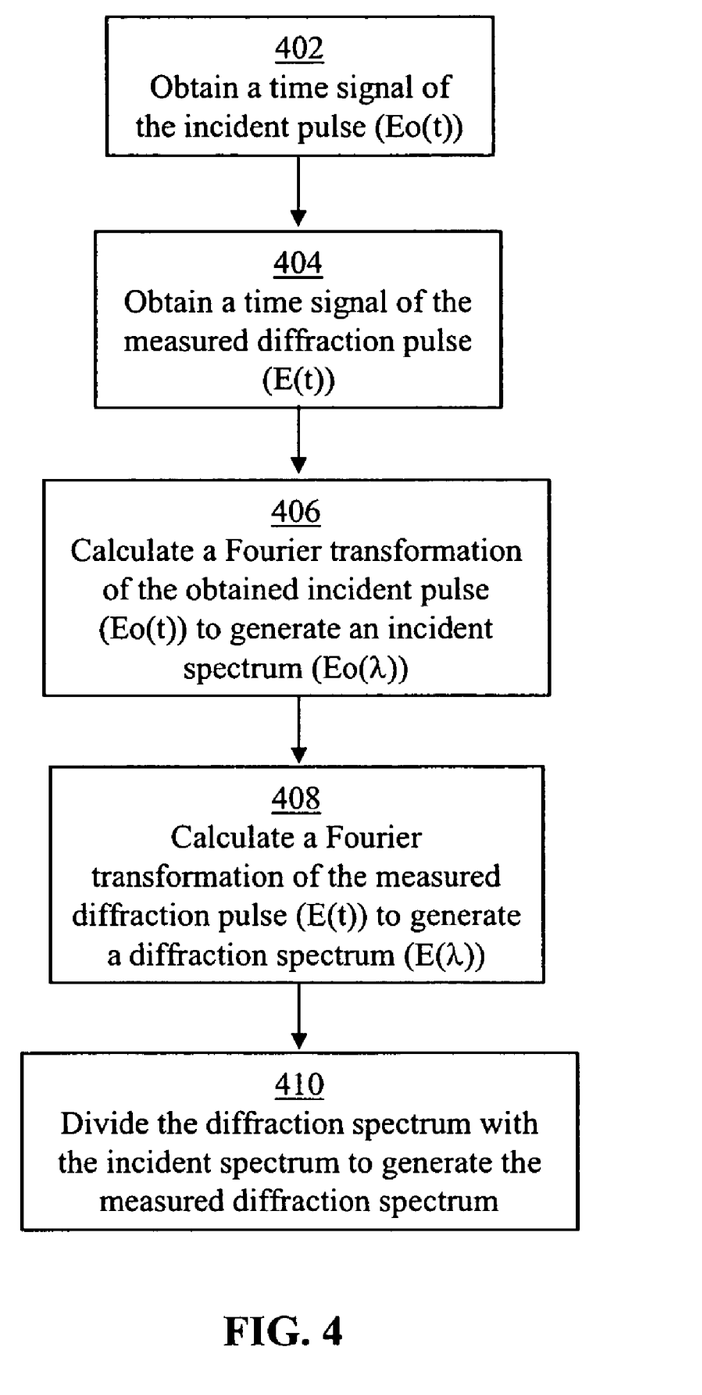
FIG. 4 depicts another exemplary process to compare a measured diffraction spectrum with a simulated diffraction pulse.

With reference to FIG. 4, an exemplary process is depicted to derive a measured diffraction spectrum from the measured diffraction pulse. In 402, a time signal of the incident pulse ($E_0(t)$) is obtained. In 404, a time signal of the measured diffraction pulse (E(t)) is obtained. In 406, a Fourier transformation of the obtained the incident pulse ($E_0(t)$) is calculated to generate an incident spectrum ($E_0(\lambda)$). In 408, a Fourier transformation of the measured diffraction pulse (E(t)) is calculated to generate a diffraction spectrum (E(λ)). In 410, the diffraction spectrum (E(λ)) is divided with the incident spectrum ($E_0(\lambda)$) to generate the measured diffraction spectrum of the structure.

4.2 Modeling of Numerical Approach

The following describes a simulation to demonstrate the numerical approach described above. This simulation assumed a Gaussian beam with a FWHM-width of 3 fs and a carrier frequency of 4 THz (corresponding to λ≈500 nm), which is diffracted by two different gratings etched in Silicon with a grating period of 500 nm, an etch depth of 200 nm and linewidths of 250 nm and 240 nm, respectively.

Figure 5:
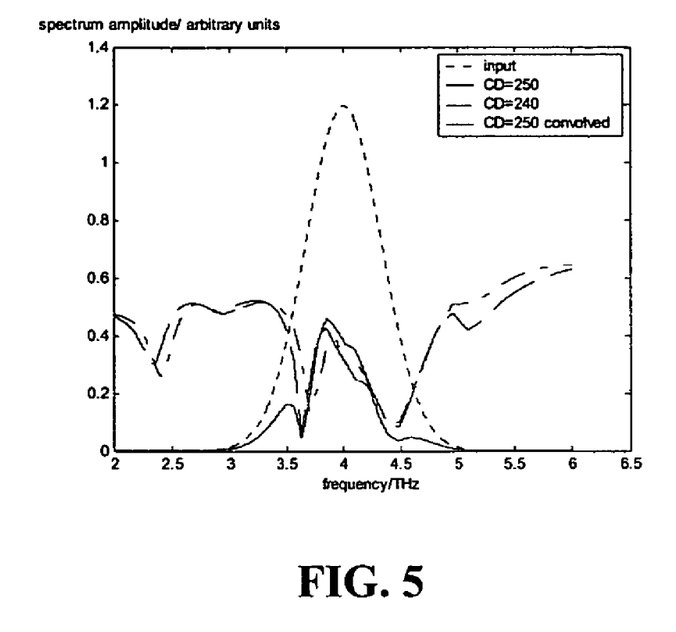
FIG. 5 depicts exemplary amplitude signals of incident pulses.

FIG. 5 depicts the simulated frequency spectra for the incident pulse as well as the response spectra for the two gratings. For the sake of convenience, only the amplitude spectra are shown. Note that the phase spectrum for the Gaussian pulse is flat (constant), while the response spectra are not. The spectrum of the pulse after being diffracted from the 250 nm grating is also shown (solid line).

Figure 6:
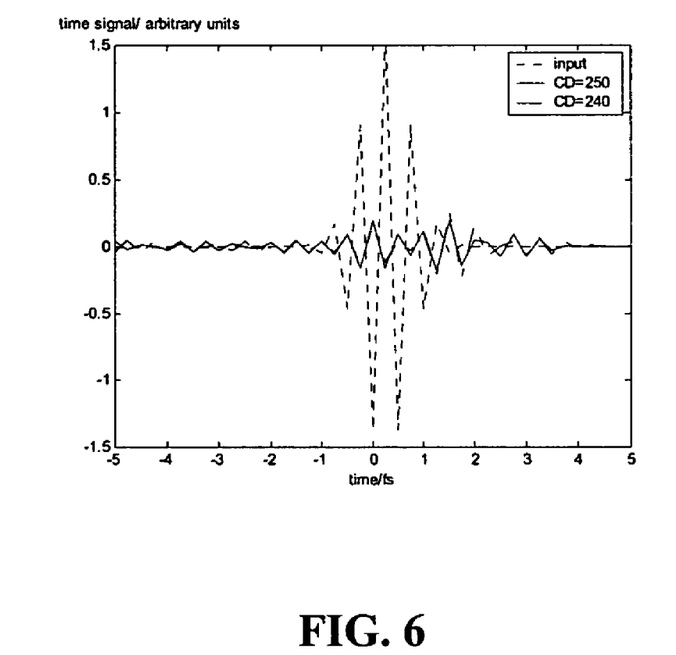
FIG. 6 depicts exemplary time signals of reflected pulses.

FIG. 6 depicts the time signals of the diffraction pulses obtained after convolution with the grating spectrum and Fourier back transformation. As can be seen in FIG. 6, the diffraction pulses are considerably distorted by the grating in relation to the incident pulse (dotted line). Moreover, slight differences in the time signal due to the different CD can be observed.

4.3 Analytic Approach

The following describes an analytic approach to analyzing the interaction of a pulse with a structure. See also, Karl Hehl: "Phase and Phase Derivative Targets" Research Report, Jena 2000. Due to the imposed application conditions (Gaussian pulse, power series development), however, it can not replace the numeric approaches described above.

For the sake of example, assume the following:

$$A_g(\omega) = \exp(i \cdot \phi(\omega)) \tag{11}$$

(i.e., the spectrum is expressed by an exponential function). The real and the imaginary part of $\phi$ are related to $A_g$ via:

$$\Re(\phi) = \arg(A_g)$$

$$\Im(\phi) = -\ln(|A_g|). \tag{12}$$

Moreover, the argument of the exponential function $\phi(\omega)$ is developed in a power series around the frequency $\omega_0$:

$$\phi(\omega) = \phi(\omega_0) + (\omega - \omega_0) \cdot \phi'(\omega_0) + \tag{13}$$
$$(\omega - \omega_0)^2 \cdot \frac{\phi''(\omega_0)}{2} + (\omega - \omega_0)^3 \cdot \frac{\phi'''(\omega_0)}{6} + \ldots$$

with $\phi'$, $\phi''$, ... being the derivations for $\omega$. With the formal replacements $\phi(\omega)_0 = \phi_0$, $\phi' = T$, $\phi'' = G$ and $\phi''' = TOP$ (i.e., the third order coefficient), the following is obtained:

$$\phi(\omega) = \phi_0 + (\omega - \omega_0) \cdot T(\omega_0) + \tag{14}$$
$$(\omega - \omega_0)^2 \cdot \frac{G(\omega_0)}{2} + (\omega - \omega_0)^3 \cdot \frac{TOP(\omega_0)}{6} + \ldots$$

Now, the power series representation of $A_g$ is introduced into the response formula and the impact of the higher order terms onto the pulse is computed.

4.3.a First Order Effect

The interaction of the pulse with a structure in the frequency domain can be described by:

$$A_o(\omega) = A_i(\omega) \cdot A_g(\omega) \tag{15}$$

with $A_i(\omega)$ being the frequency spectrum of the incident pulse, $A_o(\omega)$ being the frequency spectrum of the diffraction pulse, and $A_g(\omega)$ being the frequency spectrum of the structure.

Replacing the function $A_g(\omega)$ by the first order power series of $\exp(i \cdot \phi(\omega))$ in formula (13) leads to:

$$A_o(\omega) = \exp(i\{\phi_0 + (\omega - \omega_0) \cdot T(\omega_0)\}) \cdot A_i(\omega). \tag{16}$$

Applying formula (16) to a Gaussian incident pulse (see formula (4)) results in:

$$A_o(\omega) = \frac{\tau}{\sqrt{2\pi}} \cdot \exp\left(i\{\phi_0 + (\omega - \omega_0) \cdot T(\omega_0)\} - \frac{(\omega - \omega_0)^2 \tau^2}{2}\right). \tag{17}$$

The time behavior of the pulse can be computed by Fourier transforming formula (17) according to formula (1) and making use again of the quadratic supplement to solve the integral:

$$E(t) = e^{+i\phi_0} \cdot e^{+i\omega_0 t} \cdot e^{-\frac{1}{2}\left(\frac{t+T}{\tau}\right)^2}. \tag{18}$$

4.3.b Second Order Effect

The function $A_g(\omega)$ in formula (18) is replaced by the power series of $\exp(i \cdot \phi(\omega))$ in formula (18) up to the second order resulting in:

$$A_0(\omega) = \exp\left(i\left\{\phi_0 + (\omega - \omega_0) \cdot T(\omega_0) + (\omega - \omega_0)^2 \cdot \frac{G(\omega_0)}{2}\right\}\right) \cdot A_i(\omega). \tag{19}$$

Then, for a Gaussian incident pulse, the spectrum is:

$$A_o(\omega) = \tag{20}$$
$$\frac{\tau}{\sqrt{2\pi}} \cdot \exp\left(i\{\phi_0 + (\omega - \omega_0) \cdot T(\omega_0)\} + \frac{1}{2}(\omega - \omega_0)^2 \cdot (i \cdot G(\omega_0) - \tau^2)\right).$$

Again, the time behavior of the pulse follows from the Fourier transformation as:

$$E(t) = \frac{\tau}{\sqrt{\tau^2 - i \cdot G(\omega_0)}} e^{+i\phi_0} \cdot e^{i\omega_0 t} \cdot e^{-\frac{(t+T)^2}{2(\tau^2 - iG(\omega_0))}}. \tag{21}$$

4.4 Modeling of Analytic Approach

The following describes certain characteristic modeling examples of response behavior of diffraction pulses from a structure. The modeling examples described below assumed a $\tau = 3$ fs and $\omega_0 = 4 \cdot 10^{15}$ Hz, which corresponds to $\lambda \approx 500$ nm.

4.4.a First Order

Figure 7:
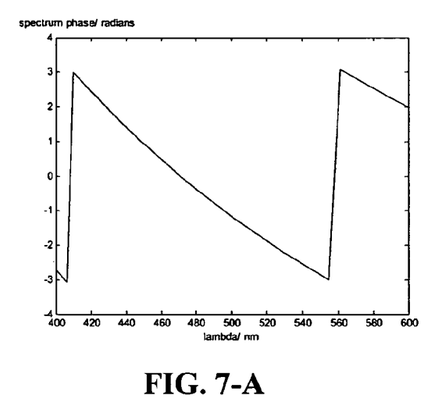

One first order effect a structure can have on an incident pulse is a time shift (T) of the diffraction pulse. Depending on the sign of T, the diffraction pulse is advanced or delayed. For example, FIGS. 7-A to 7-D depict time shifting of an incident pulse by a structure. The amplitude of the spectral response of the structure is constant at 1 over the frequency range, i.e., the reflection efficiency is 100% everywhere. The spectral phase behavior is depicted in FIGS. 7-A and 7-C. As depicted in FIGS. 7-A and 7-B, when T is positive (T=5), the resulting diffraction pulse is advanced. As depicted in FIGS. 7-C and 7-D, when T is negative (T=−5), the resulting diffraction pulse is delayed.

Figure 8:
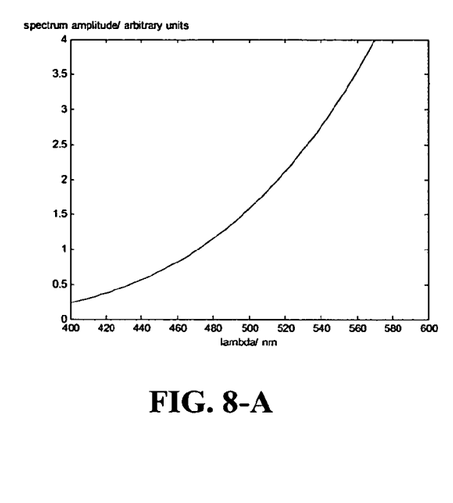

Another first-order effect a structure can have on an incident pulse is an amplitude change (T) without a phase change. For example, FIGS. 8-A to 8-D depict an amplitude change in an incident pulse by a structure. As depicted in FIGS. 8-A and 8-B, when T is positive (T=j*2), the resulting diffraction pulse is stretched, while keeping its Gaussian shape as well as its carrier frequency $\omega_0$. As depicted in FIGS. 8-C and 8-D, when T is negative (T=−j*2), the resulting diffraction pulse is compressed, while keeping its Gaussian shape as well as its carrier frequency $\omega_0$.

Note that the depiction of an amplitude greater than 1 in FIGS. 8-A to 8-D is hypothetical. Also note that the frequency behavior in FIGS. 7-A to 7-D and 8-A to 8-D would be linear rather than inverse if plotted versus the frequency instead of the wavelength.

4.4.b Second Order

In order to show the pure second order impact, the first order term T is set to zero. The second order effect is governed by the term G (see formulas 19-21). Again, the phase and the amplitude impact are considered separately.

Figure 9:
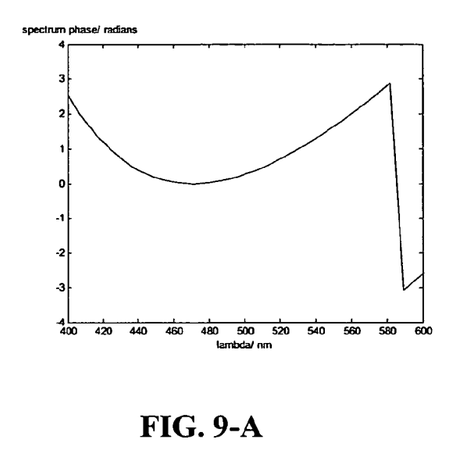

FIGS. 9-A to 9-D depict that a phase change leads to a stretching of the incident pulse. In addition, the phase of the time signal is changed with the time resulting in a continuous change of the carrier frequency, which is called "chirp." As depicted in FIGS. 9-A and 9-B, when the frequency decreases with time, the change is called a "down-chirp." As depicted in FIGS. 9-C and 9-D, when the frequency increases with time, the change is called an "up-chirp." In both cases, the resulting diffraction pulse is stretched, while keeping the Gaussian envelope shape.

Figure 10:
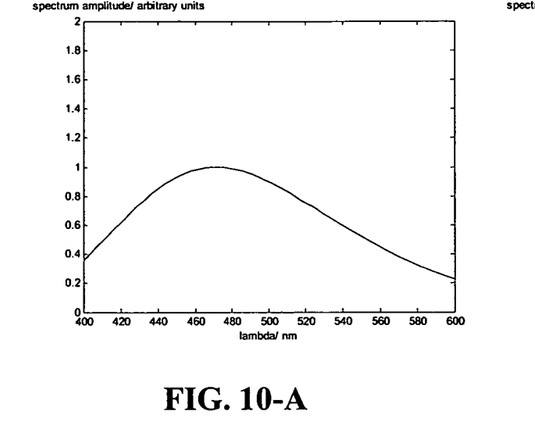

FIGS. 10-A to 10-D depict the result of a second order (quadratic) amplitude change. FIGS. 10-A and 10-B depict an amplitude attenuation of the incident pulse. FIGS. 10-C and 10-D depict an amplification of the incident pulse. Again, note that an amplitude above 1 is hypothetically.

5. Library-based Process

As described above, in one exemplary embodiment, to determine a characteristic of the profile of a structure being examined, the measured diffraction pulse is compared to a simulated diffraction pulse, which is associated with a hypothetical profile of the structure. The simulated diffraction pulse is generated, in part, by obtaining a spectral response of the structure, which is associated with the hypothetical profile of the structure.

Figure 11:
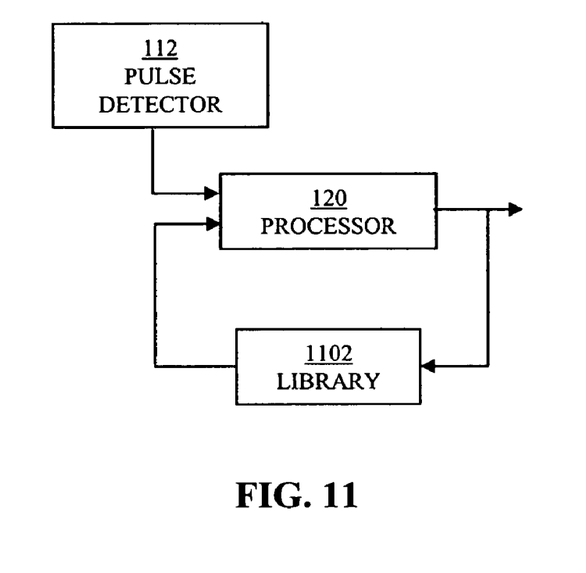
FIG. 11 depicts a library-based process of determining a characteristic of a profile of a structure being examined.

Thus, in this exemplary embodiment, with reference to FIG. 11, the spectral response and the associated hypothetical profile are obtained from a library 1102 of spectral responses and hypothetical profiles. In particular, each spectral response in library 1102 is associated with a hypothetical profile of the structure. Thus, after obtaining a measured diffraction pulse, processor 120 then compares the measured diffraction pulse to simulated diffraction pulses generated from spectral responses stored in library 1102. When the measured diffraction pulse and one of the simulated diffraction pulses generated from spectral responses in library 1102 match within a matching criterion, the hypothetical profile associated with the matching simulated diffraction pulse can be presumed to represent the actual profile of the structure being examined.

As also described above, in another exemplary embodiment, a measured diffraction spectrum is derived from the measured diffraction pulse. The measured diffraction spectrum is compared with a simulated diffraction spectrum, which is associated with a hypothetical profile of the structure.

Thus, in this exemplary embodiment, the simulated diffraction spectrum and the associated hypothetical profile are obtained from a library 1102 of simulated diffraction spectra and hypothetical profiles. In particular, each simulated diffraction spectrum in library 1102 is associated with a hypothetical profile of the structure. Thus, after obtaining a measured diffraction pulse and deriving a measured diffraction spectrum, processor 120 then compares the measured diffraction spectrum to simulated diffraction spectra stored in library 1102. When the measured diffraction spectrum and one of the simulated diffraction spectra in library 1102 match within a matching criterion, the hypothetical profile associated with the matching simulated diffraction spectrum can be presumed to represent the actual profile of the structure being examined.

The set of hypothetical profiles stored in library 1102 can be generated by characterizing a hypothetical profile using a set of parameters, then varying the set of parameters to generate hypothetical profiles of varying shapes and dimensions. The process of characterizing a profile using a set of parameters can be referred to as parameterizing.

Figure 12:
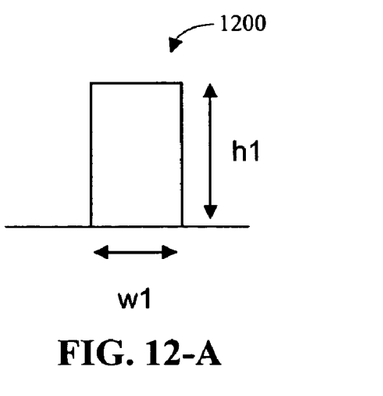

For example, as depicted in FIG. 12-A, assume that hypothetical profile 1200 can be characterized by parameters h1 and w1 that define its height and width, respectively. As depicted in FIGS. 12-B to 12-E, additional shapes and features of hypothetical profile 1200 can be characterized by increasing the number of parameters. For example, as depicted in FIG. 12-B, hypothetical profile 1200 can be characterized by parameters h1, w1, and w2 that define its height, bottom width, and top width, respectively. Note that the width of hypothetical profile 1200 can be referred to as the critical dimension (CD). For example, in FIG. 12-B, parameter w1 and w2 can be described as defining the bottom CD and top CD, respectively, of hypothetical profile 1100.

As described above, the set of hypothetical profiles stored in library 1102 (FIG. 11) can be generated by varying the parameters that characterize the hypothetical profile. For example, with reference to FIG. 12-B, by varying parameters h1, w1, and w2, hypothetical profiles of varying shapes and dimensions can be generated. Note that one, two, or all three parameters can be varied relative to one another.

For a more detailed description of a library-based process, see U.S. patent application Ser. No. 09/907,488, titled GENERATION OF A LIBRARY OF PERIODIC GRATING DIFFRACTION SIGNALS, filed on Jul. 16, 2001, which is incorporated herein by reference in its entirety.

6. Regression-based Process

Figure 13:
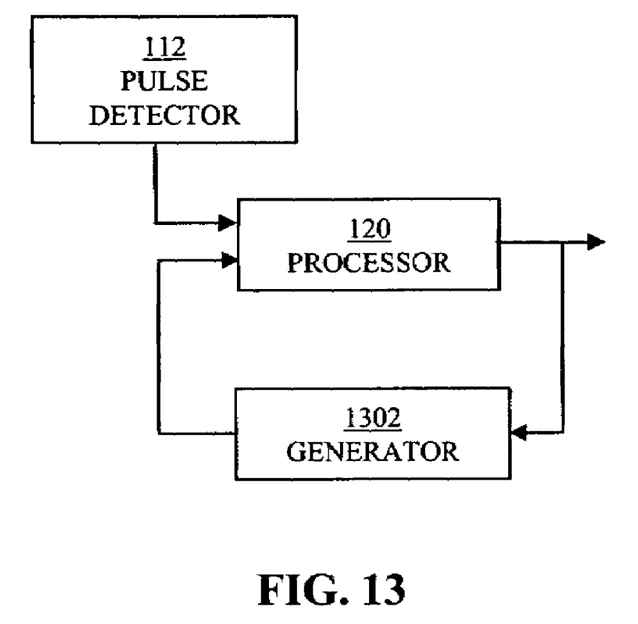
FIG. 13 depicts a regression-based process of determining a characteristic of a profile of a structure being examined.

Rather than using library 1102, the spectral response/ simulated diffraction spectrum and associated hypothetical profile can be obtained using a regression-based process. With reference to FIG. 13, a spectral response/simulated diffraction spectrum is generated using a spectral response/ simulated diffraction signal generator 1302.

In particular, in the exemplary embodiment where the measured diffraction pulse is compared to a simulated diffraction pulse, if the measured diffraction pulse and the simulated diffraction pulse do not match within a matching criterion, another spectral response is generated using another set of parameters for another hypothetical profile. Another simulated diffraction pulse is generated using the newly generated spectral response, then compared to the measured diffraction pulse.

In the exemplary embodiment, where a measured diffraction spectrum, which is derived from the measured diffraction pulse, is compared with a simulated diffraction spectrum, if the measured diffraction spectrum and the simulated diffraction spectrum do not match within a matching criterion, another simulated diffraction spectrum is generated using another set of parameters for another hypothetical profile. The newly generated simulated diffraction spectrum is then compared to the measured diffraction spectrum.

Note that the subsequently generated spectral response/ simulated diffraction spectrum can be generated using an optimization algorithm, such as global optimization techniques, which includes simulated annealing, and local optimization techniques, which includes steepest descent algorithm.

For a more detailed description of a regression-based process, see U.S. patent application Ser. No. 09/923,578, titled METHOD AND SYSTEM OF DYNAMIC LEARNING THROUGH A REGRESSION-BASED LIBRARY GENERATION PROCESS, filed on Aug. 6, 2001, which is incorporated herein by reference in its entirety.

7. Numerical Analysis Techniques

In one exemplary embodiment, spectral responses/simulated diffraction spectra can be generated by applying Maxwell's equations and using a numerical analysis technique to solve Maxwell's equations. More particularly, in the exemplary embodiment described below, RCWA is used. It should be noted, however, that various numerical analysis techniques, including variations of RCWA, modal analysis, integral method, Green's functions, Fresnel method, finite element and the like can be used.

In general, RCWA involves dividing a profile into a number of sections, slices, or slabs (hereafter simply referred to as sections). For each section of the profile, a system of coupled differential equations generated using a Fourier expansion of Maxwell's equations (i.e., the components of the electromagnetic field and permittivity ($\epsilon$)). The system of differential equations is then solved using a diagonalization procedure that involves eigenvalue and eigenvector decomposition (i.e., Eigen-decomposition) of the characteristic matrix of the related differential equation system. Finally, the solutions for each section of the profile are coupled using a recursive-coupling schema, such as a scattering matrix approach. For a description of a scattering matrix approach, see Lifeng Li, "Formulation and comparison of two recursive matrix algorithms for modeling layered diffraction gratings," J. Opt. Soc. Am. A13, pp 1024-1035 (1996), which is incorporated herein by reference in its entirety. Specifically for a more detail description of RCWA, see U.S. patent application Ser. No. 09/770,997, titled CACHING OF INTRA-LAYER CALCULATIONS FOR RAPID RIGOROUS COUPLED-WAVE ANALYSES, filed on Jan. 25, 2001, which is incorporated herein by reference in its entirety.

8. Machine Learning Systems

Figure 14:
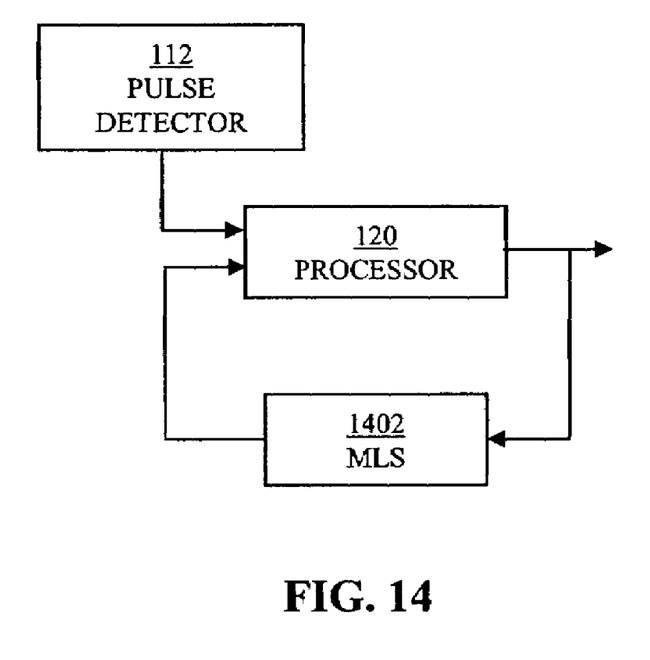
FIG. 14 depicts a machine-learning-system-based process of determining a characteristic of a profile of a structure being examined.

With reference to FIG. 14, in one exemplary embodiment, spectral responses/simulated diffraction spectra can be generated using a machine learning system (MLS) 1402, which employs a machine learning algorithm, such as back-propagation, radial basis function, support vector, kernel regression, and the like. For a more detailed description of machine learning systems and algorithms, see "Neural Networks" by Simon Haykin, Prentice Hall, 1999, which is incorporated herein by reference in its entirety. See also U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching.

We claim:

1. A method of examining a structure formed on a wafer, the structure having a profile, the method comprising:
   directing an incident pulse at the structure, wherein the incident pulse is a sub-picosecond optical pulse;
   measuring a diffraction pulse resulting from the incident pulse diffracting from the structure;
   obtaining a time signal of the incident pulse ($E_o(t)$);
   convolving the time signal of the incident pulse ($E_o(t)$) with an impulse response ($G(t-\tau)$) of the structure to generate a simulated diffraction pulse;
   comparing the measured diffraction pulse to the simulated diffraction pulse, wherein a hypothetical profile of the structure is associated with the simulated diffraction pulse; and
   when the pulses match within a matching criterion, determining a characteristic of the profile of the structure based on the hypothetical profile of the structure associated with the simulated diffraction pulse that matched the measured diffraction pulse.

2. The method of claim 1, wherein measuring the diffraction pulse includes auto-correlating the diffraction pulse, which comprises:
   splitting the diffraction pulse into two pulses;
   time delaying the pulses; and
   superimposing the delayed pulses.

3. The method of claim 2, wherein auto-correlating the diffraction pulse includes using a frequency-resolved optical grating.

4. The method of claim 2, wherein auto-correlating the diffraction pulse includes using spectral phase interferometry for direct electric field reconstruction, which comprises:
   generating two replicas of the diffraction pulse;
   time delaying the replicas with respect to one another by $\tau$;
   stretching another pulse (a chirped pulse) to a duration longer than $\tau$;
   mixing the replicas with the chirped pulse in a nonlinear medium to generate a resultant signal; and
   resolving the resultant signal with a spectrometer.

5. The method of claim 1, wherein measuring the diffraction pulse includes cross-correlating the diffraction pulse, which comprises:
   measuring a reference pulse; and
   comparing the diffraction pulse and the reference pulse.

6. The method of claim 5, wherein the reference pulse is measured from the incident pulse.

7. The method of claim 1, wherein convolving the time signal of the incident pulse ($E_o(t)$) with an impulse response ($G(t-\tau)$) of the structure comprises:
   calculating a Fourier transformation of the obtained time signal to generate an incident spectrum ($E_o(v)$);
   obtaining a frequency response ($G(v)$) of the structure;
   multiplying the incident spectrum ($E_o(v)$) with the frequency response ($G(v)$) to generate a diffraction spectrum ($E(v)$); and
   calculating a back-Fourier transformation of the diffraction spectrum ($E(v)$) to generate the simulated diffraction pulse.

8. The method of claim 7, further comprising:
   obtaining a spectral response ($G(\lambda)$) of the structure; and
   translating the spectral response ($G(\lambda)$) into the frequency response ($G(v)$).

9. The method of claim 8, wherein the spectral response ($G(\lambda)$) of the structure is obtained from a library of spectral responses, wherein each spectral response in the library is associated with a different hypothetical profile of the structure.

10. The method of claim 8, wherein the spectral response ($G(\lambda)$) of the structure is generated prior to comparing the simulated diffraction pulse with the measured diffraction pulse, and wherein, when the measured diffraction pulse and the simulated diffraction pulse do not match within the matching criterion, another spectral response for a different hypothetical profile of the structure is generated.

11. The method of claim 8, wherein the spectral response is generated using a numerical analysis technique.

12. The method of claim 8, wherein the spectral response is generated using a machine learning system.

13. A method of examining a structure formed on a wafer, the structure having a profile, the method comprising:
   directing an incident pulse at the structure, wherein the incident pulse is a sub-picosecond optical pulse;
   measuring a diffraction pulse resulting from the incident pulse diffracting from the structure;
   deriving a measured diffraction spectrum from the measured diffraction pulse;
   comparing the measured diffraction spectrum to a simulated diffraction spectrum,
   wherein a hypothetical profile of the structure is associated with the simulated diffraction spectrum; and
   when the spectra match within a matching criterion, determining a characteristic of the profile of the structure based on the hypothetical profile of the structure associated with the simulated diffraction spectrum that matched the measured diffraction spectrum.

14. The method of claim 13, wherein deriving a measured diffraction spectrum comprises:
   obtaining a time signal of the incident pulse ($E_o(t)$);
   obtaining a time signal of the measured diffraction pulse ($E(t)$);
   calculating a Fourier transformation of the obtained incident pulse ($E_o(t)$) to generate an incident spectrum ($E_o(\lambda)$);
   calculating a Fourier transformation of the measured diffraction pulse ($E(t)$) to generate a diffraction spectrum ($E(\lambda)$); and
   dividing the diffraction spectrum ($E(\lambda)$) with the incident spectrum ($E_o(\lambda)$) to generate the measured diffraction spectrum of the structure.

15. The method of claim 13, wherein the simulated diffraction spectrum is obtained from a library of simulated diffraction spectra, wherein each simulated diffraction spectrum in the library is associated with a different hypothetical profile of the structure.

16. The method of claim 13, wherein the simulated diffraction spectrum is generated prior to comparing the simulated diffraction spectrum with the measured diffraction spectrum, and wherein, when the measured diffraction spectrum and the simulated diffraction spectrum do not match within the matching criterion, another simulated diffraction spectrum for a different hypothetical profile of the structure is generated.

17. The method of claim 13, wherein the simulated diffraction spectrum is generated using a numerical analysis technique.

18. The method of claim 13, wherein the simulated diffraction spectrum is generated using a machine learning system.

19. A system to examine a structure formed on a wafer, the structure having a profile, the system comprising:
   a pulse generator configured to direct an incident pulse at the structure, wherein the incident pulse is a sub-picosecond optical pulse;
   a pulse detector configured to measure a diffraction pulse resulting from the incident pulse diffracting from the structure;
   a processor configured to determine a characteristic of the profile of the structure based on the measured diffraction pulse; and
   a simulated diffraction signal generator, wherein the processor is configured to derive a measured diffraction spectrum from the measured diffraction pulse and compare the measured diffraction spectrum to a simulated diffraction signal generated by the simulated diffraction signal generator.

20. The system of claim 19, further comprising:
   a library of spectral responses and hypothetical profiles of the structure, wherein each spectral response in the library is associated with a different hypothetical profile of the structure, and wherein the processor is configured to generate a simulated diffraction pulse using a spectral response from the library and compare the measured diffraction pulse to the simulated diffraction pulse.

21. The system of claim 19, further comprising:
   a spectral response generator, wherein the processor is configured to generate a simulated diffraction pulse using a spectral response generated by the spectral response generator and compare the measured diffraction pulse to the simulated diffraction pulse.

22. A system to examine a structure formed on a wafer, the structure having a profile, the system comprising:
   a pulse generator configured to direct an incident pulse at the structure, wherein the incident pulse is a sub-picosecond optical pulse;
   a pulse detector configured to measure a diffraction pulse resulting from the incident pulse diffracting from the structure;
   a processor configured to determine a characteristic of the profile of the structure based on the measured diffraction pulse; and
   a library of simulated diffraction spectra and hypothetical profiles of the structure, wherein each simulated diffraction spectrum in the library is associated with a different hypothetical profile of the structure, and wherein the processor is configured to derive a measured diffraction spectrum from the measured diffraction pulse and compare the measured diffraction spectrum to a simulated diffraction spectrum from the library.

23. A computer-readable storage medium containing computer executable instructions for causing a computer to examine a structure formed on a wafer, the structure having a profile, comprising instructions for:
   measuring a diffraction pulse resulting from an incident pulse diffracting from the structure, wherein the incident pulse is a sub-picosecond optical pulse;
   obtaining a time signal of the incident pulse ($E_o(t)$);
   convolving the time signal of the incident pulse ($E_o(t)$) with an impulse response ($G(t-\tau)$) of the structure to generate a simulated diffraction pulse;
   comparing the measured diffraction pulse to the simulated diffraction pulse, wherein a hypothetical profile of the structure is associated with the simulated diffraction pulse; and when the pulses match within a matching criterion, determining a characteristic of the profile of the structure based on the hypothetical profile of the structure associated with the simulated diffraction pulse that matched the measured diffraction pulse.

24. The computer-readable storage medium of claim 23, wherein instructions for convolving the time signal of the incident pulse ($E_o(t)$) with an impulse response ($G(t-\tau)$) of the structure comprises instructions for:
 calculating a Fourier transformation of the obtained time signal to generate an incident spectrum ($E_o(v)$);
 obtaining a frequency response ($G(v)$) of the structure;
 multiplying the incident spectrum ($E_o(v)$) with the frequency response ($G(v)$) to generate a diffraction spectrum ($E(v)$); and
 calculating a back-Fourier transformation of the diffraction spectrum ($E(v)$) to generate the simulated diffraction pulse.

25. The computer-readable storage medium of claim 24, further comprising instructions for:
 obtaining a spectral response ($G(v)$) of the structure; and
 translating the spectral response ($G(v)$) into the frequency response ($G(v)$).

26. A computer-readable storage medium containing computer executable instructions for causing a computer to examine a structure formed on a wafer, the structure having a profile, comprising instructions for:
 measuring a diffraction pulse resulting from an incident pulse diffracting from the structure, wherein the incident pulse is a sub-picosecond optical pulse;
 deriving a measured diffraction spectrum from the measured diffraction pulse;
 comparing the measured diffraction spectrum to a simulated diffraction spectrum,
 wherein a hypothetical profile of the structure is associated with the simulated diffraction spectrum; and
 when the spectra match within a matching criterion, determining a characteristic of the profile of the structure based on the hypothetical profile of the structure associated with the simulated diffraction spectrum that matched the measured diffraction spectrum.

27. The computer-readable storage medium of claim 26, wherein instructions for deriving a measured diffraction spectrum comprises instructions for:
 obtaining a time signal of the incident pulse ($E_o(t)$);
 obtaining a time signal of the measured diffraction pulse ($E(t)$);
 calculating a Fourier transformation of the obtained incident pulse ($E_o(t)$) to generate an incident spectrum ($E_o(\lambda)$);
 calculating a Fourier transformation of the measured diffraction pulse ($E(t)$) to generate a diffraction spectrum ($E(\lambda)$); and
 dividing the diffraction spectrum ($E(\lambda)$) with the incident spectrum ($E_o(\lambda)$) to generate the measured diffraction spectrum of the structure.

* * * * *